(12) United States Patent
Jang et al.

(10) Patent No.: US 8,018,800 B2
(45) Date of Patent: Sep. 13, 2011

(54) OPTICAL RECORDING AND/OR REPRODUCING APPARATUS HAVING A HIGH-SENSITIVITY MAGNETIC CIRCUIT

(75) Inventors: Dae-jong Jang, Anyang-si (KR);
Byung-youn Song, Suwon-si (KR);
Pyong-yong Seong, Seoul (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 1732 days.

(21) Appl. No.: 11/012,732

(22) Filed: Dec. 16, 2004

(65) Prior Publication Data

US 2005/0185531 A1     Aug. 25, 2005

(30) Foreign Application Priority Data

Dec. 17, 2003   (KR) .................. 10-2003-0092591

(51) Int. Cl.
*G11B 7/00* (2006.01)
(52) U.S. Cl. ................... 369/44.22; 369/44.21
(58) Field of Classification Search .......... 720/681, 720/683; 369/44.11, 44.15, 44.21, 44.22; 359/813, 824
See application file for complete search history.

(56) References Cited

U.S. PATENT DOCUMENTS

| | | | | |
|---|---|---|---|---|
| 5,949,590 | A * | 9/1999 | Hong | 359/814 |
| 6,343,053 | B1 * | 1/2002 | Akanuma et al. | 369/44.14 |
| 6,791,772 | B2 * | 9/2004 | Wakabayashi et al. | 359/824 |
| 2003/0128443 | A1 * | 7/2003 | Jang et al. | 359/824 |

FOREIGN PATENT DOCUMENTS

| | | |
|---|---|---|
| EP | 1 355 301 A2 | 10/2003 |
| EP | 1 355 301 A3 | 3/2006 |
| JP | 1996-263861 | 10/1996 |
| JP | 2000-207757 | 7/2000 |
| JP | 2001-167458 | 6/2001 |
| JP | 2002-092916 | 3/2002 |
| JP | 2002-140828 | 5/2002 |
| JP | 2002-245647 | 8/2002 |
| JP | 2003-015009 | 1/2003 |
| JP | 2003-203373 | 7/2003 |

(Continued)

OTHER PUBLICATIONS

European Search Report for Application No. 04257877.3, mailed Apr. 12, 2006.
Japanese Office Action for Application No. 2004-365082; dated Jul. 11, 2006.

(Continued)

*Primary Examiner* — William J Klimowicz
*Assistant Examiner* — Kim-Kwok Chu
(74) *Attorney, Agent, or Firm* — Staas & Halsey LLP

(57) ABSTRACT

A magnetic circuit and an optical recording and/or reproducing apparatus employing the magnetic circuit, having: a magnet with first and second magnetic portions adjacent to each other and opposite in polarity, and third and fourth magnetic portions surrounding the first and second magnetic portions, respectively, and have opposite polarities to the first and second magnetic portions, respectively; and at least one of a tracking coil unit or a focus coil unit. The tracking coil unit has first through third tracking coils arranged in a tracking direction so that each tracking coil interacts with two of the first through fourth magnetic portions. The focus coil unit has first through fourth focus coils, two of which are disposed in a focus direction to interact with the first and third magnetic portions, and the remaining two of which are disposed in the focus direction to interact with second and fourth magnetic portions.

43 Claims, 4 Drawing Sheets

FOREIGN PATENT DOCUMENTS

| | | |
|---|---|---|
| JP | 2003-272201 | 9/2003 |
| TW | 160032 | 6/1991 |
| TW | 455845 | 9/2001 |
| TW | 476944 | 2/2002 |

OTHER PUBLICATIONS

Taiwanese Office Action for corresponding Taiwanese application 093138097; dated Jun. 23, 2009.

* cited by examiner

OPTICAL RECORDING AND/OR REPRODUCING APPARATUS HAVING A HIGH-SENSITIVITY MAGNETIC CIRCUIT

CROSS-REFERENCE TO RELATED APPLICATIONS

This application claims the priority of Korean Patent Application No. 2003-92591, filed on Dec. 17, 2003, in the Korean Intellectual Property Office, the disclosure of which is incorporated herein by reference.

BACKGROUND OF THE INVENTION

1. Field of the Invention

The present invention relates to an optical recording and/or reproducing apparatus, and more particularly, to a high-sensitivity magnetic circuit and an optical recording and/or reproducing apparatus employing the same.

2. Description of the Related Art

In general, an optical recording and/or reproducing apparatus employs an optical pickup to perform non-contact recording and/or reproducing of information on an optical disc, which is an optical information storage medium, while moving in a radial direction of the optical disc.

An optical pickup needs an actuator that drives an objective lens in tracking, focus, and/or tilt directions, so that a beam emitted by a light source is focused to a spot at the proper position on an optical disc. Here, driving the objective lens in a tracking direction means controlling movement of the objective lens in a radial direction of the optical disc, so that a beam spot is positioned at a center of a track.

A typical optical pickup actuator includes a bobbin mounted movably on a base, a suspension that supports the bobbin so that the bobbin is movable with respect to the base, and a pair of magnetic circuits disposed opposite each other on the bobbin and the base, respectively.

An optical pickup actuator basically performs two-axis control in the tracking direction and the focus direction. There is increasing demand for a high-density, small-size, and lightweight optical recording and/or reproducing apparatus.

To achieve high density, an optical pickup actuator needs to perform three- or four-axis control, including tilt control, in addition to two-axis control.

In recent years, a numerical aperture (NA) of an objective lens has increased and the wavelength of a light source has decreased for realization of high-density optical storage devices, which decreases a tilt margin of an optical pickup actuator. To compensate for this, there is a need for an optical pickup actuator designed to perform three- or four-axis control, including tilt control, in addition to tracking and focusing control. Three-axis control means control in focus, tracking, and radial tilt directions, and four-axis control means control in focus, tracking, radial tilt, and tangential tilt directions. Whether the optical pickup actuator can perform two-axis, three-axis, or four-axis control is determined by the structure of a magnetic circuit.

Furthermore, to meet the increasing demand for high speed, there is a need for an optical pickup actuator with improved sensitivity. High-density optical information storage media currently under development, some of which are already commercially available, such as Blu-ray discs (BDs), require an optical pickup actuator with even higher sensitivity than required by CDs or DVDs. For example, a four-speed optical recording and/or reproducing apparatus for BDs needs an optical pickup actuator that is at least as sensitive as an optical pickup actuator of a 16-speed optical recording and/or reproducing apparatus for recordable DVDs.

However, the highest sensitivity available in an optical pickup actuator at present is comparable to that required for 16-speed recordable DVDs. One of the biggest problems encountered in realizing high-speed BDs is that the sensitivity of an optical pickup actuator must also be increased.

Thus, to realize a higher-speed optical recording and/or reproducing apparatus for BDs and/or DVDs, a novel optical pickup actuator with improved sensitivity is highly desirable.

FIG. 4 schematically shows an example of a conventional magnetic circuit that can be used for a 52-speed CD-ROM. FIG. 5 shows another example of a conventional magnetic circuit that can be applied to a 16-speed DVD-ROM. For better visualization, the focus coil is not shown in FIGS. 4 and 5, in which horizontal and vertical directions are tracking and focus directions, respectively.

The conventional magnetic circuit of FIG. 4 includes a unipolar magnet 131 and a pair of tracking coils 140. In this magnetic circuit, only about a fourth of the tracking coils 140 is used for tracking control. It is known that the magnetic circuit constructed as shown in FIG. 4 offers tracking sensitivity of about 40-50 μm/V. Here, V means volt.

The conventional magnetic circuit of FIG. 5 includes a magnet 231 having first and second magnetic portions 233 and 235 magnetized with opposite polarities, and a tracking coil 240 that interacts with the magnet 231. In this magnetic circuit, about a half of the tracking coil 240 is used for tracking control. It is known that the magnetic circuit constructed as shown in FIG. 5 offers tracking sensitivity of about 60-70 μm/V.

As shown in FIG. 5, it is impossible to utilize the tracking coil more efficiently by using more than two sides of the tracking coil 240 for tracking control. Thus, tracking sensitivity can only be improved by increasing the number of tracking coils.

SUMMARY OF THE INVENTION

The present invention provides a magnetic circuit designed to provide a high sensitivity comparable to that required in a high-speed optical recording and/or reproducing apparatus, and an optical recording and/or reproducing apparatus employing the same.

According to an aspect of the present invention, there is provided a magnetic circuit for an optical pickup actuator, comprising: a magnet including first and second magnetic portions that are adjacent to each other and opposite in polarity, and third and fourth magnetic portions that surround the first and second magnetic portions, respectively, and have opposite polarities to the first and second magnetic portions, respectively, and a tracking coil unit including first through third tracking coils arranged in a first direction so that each tracking coil interacts with two of the first through fourth magnetic portions.

According to one aspect, the magnetic circuit further comprises a focus coil unit that includes first through fourth focus coils, two of which are disposed on opposing sides of the tracking coil unit in a second direction crossing the first direction to interact with the first and third magnetic portions, and the remaining two of which are disposed on the opposing sides of the tracking coil unit in the second direction to interact with second and fourth magnetic portions.

According to one aspect, each of the first through third tracking coils has a multilayer structure.

According to another aspect, the magnetic circuit comprises a magnet including first and second magnetic portions that are adjacent to each other and opposite in polarity, and third and fourth magnetic portions that surround the first and second magnetic portions, respectively, and have opposite polarities to the first and second magnetic portions, respectively, and a focus coil unit that includes first through fourth focus coils, two of which are disposed in a focus direction to interact with the first and third magnetic portions, and the remaining two of which are disposed in the focus direction to interact with second and fourth magnetic portions.

According to one aspect, each of the first through fourth focus coils has a multilayer structure.

According to one aspect, the focus coil unit is used for focus and tilt driving.

According to one aspect, the magnetic circuit further includes a tilt coil unit having first through fourth tilt coils that overlap with the first through fourth focus coils, respectively.

According to one aspect, each of the first through fourth tilt coils has a multilayer structure.

According to one aspect, the track coils are made of fine pattern coils. According to one aspect, the focus coils are made of fine pattern coils. According to one aspect, the tilt coils are made of fine pattern coils.

According to one aspect, the magnet is a quadrupole magnet, or a magnet formed by attaching a surface two-pole magnet having the first and third magnetic portions to another surface two-pole magnet having the second and fourth magnetic portions.

According to another aspect of the present invention, there is provided an optical recording and/or reproducing apparatus comprising: an optical pickup which has an actuator driving an objective lens, which is installed capable of movement along a radial direction of an optical information storage medium, and which reproduces and/or records information on the optical information storage medium; and a controller that controls servos of the optical pickup, wherein the actuator consists of a lens holder holding an objective lens, a plurality of supports that support the lens holder movably with respect to a base, each of the supports having a first end attached to one of two opposing sides of the lens holder and a second end fixed to a holder mounted on one side of the base, and a pair of magnetic circuits disposed opposite each other on remaining opposing sides of the lens holder to which the supports are not attached and the base. At least one of the pair of magnetic circuits includes a magnet having first and second magnetic portions that are adjacent to each other and opposite in polarity, and third and fourth magnetic portions that surround the first and second magnetic portions, respectively, and have opposite polarities to the first and second magnetic portions, respectively, and a tracking coil unit including first through third tracking coils arranged in a first direction so that each tracking coil interacts with two of the first through fourth magnetic portions.

According to one aspect, the magnetic circuit further comprises a focus coil unit that includes first through fourth focus coils, two of which are disposed on opposing sides of the tracking coil unit in a second direction crossing the first direction to interact with the first and third magnetic portions, and the remaining two of which are disposed on the opposing sides of the tracking coil unit in the second direction to interact with second and fourth magnetic portions.

According to another aspect, the magnetic circuit in the optical recording and/or reproducing apparatus includes a magnet including first and second magnetic portions that are adjacent to each other and opposite in polarity, and third and fourth magnetic portions that surround the first and second magnetic portions and have opposite polarities to the first and second magnetic portions, respectively, and a focus coil unit that includes first through fourth focus coils, two of which are disposed in a focus direction to interact with the first and third magnetic portions, and the remaining two of which are disposed in the focus direction to interact with second and fourth magnetic portions.

According to one aspect, the focus coil unit is used for focus and tilt driving.

According to one aspect, the magnetic circuit further comprises a tilt coil unit including first through fourth tilt coils that overlap with the first through fourth focus coils, respectively.

Additional aspects and/or advantages of the invention will be set forth in part in the description which follows, and in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings, of which.

DETAILED DESCRIPTION

Figure 1:
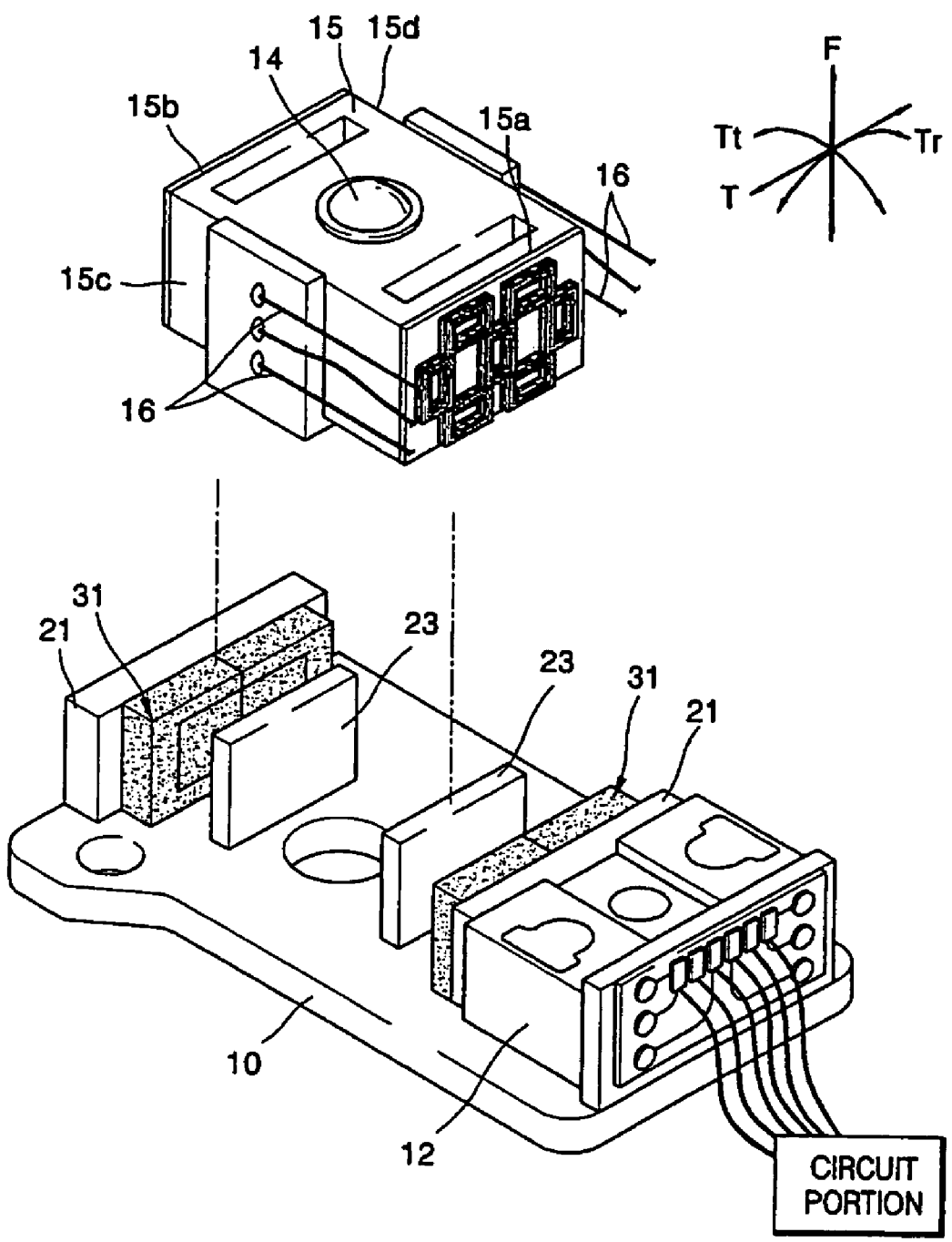
FIG. 1 is a schematic perspective view of an optical pickup actuator employing a magnetic circuit according to the present invention.

Reference will now be made in detail to embodiments of the present invention, examples of which are illustrated in the accompanying drawings, wherein like reference numerals refer to the like elements throughout. The embodiments are described to explain the present invention by referring to the figures.

In FIG. 1, F, T, Tr, and Tt denote focus direction, tracking direction (corresponding to a radial direction of a disc-like optical information storage medium), radial tilt direction, and tangential tilt direction, respectively.

Referring to FIG. 1, an optical pickup actuator according to an embodiment of the present invention includes a lens holder 15 that is movably mounted on a base 10 and holds an objective lens 14, a plurality of supports 16 that support the lens holder 15 to be movable with respect to the base 10, each with a first end attached to one of two sides 15c and 15d of the lens holder 15 and a second end fixed to a holder 12 mounted on one side of the base 10, and a pair of magnetic circuits disposed opposite each other on one of remaining sides 15a and 15b of the lens holder 15 and the base 10.

The optical pickup actuator may further include either or both internal yokes 23 and external yokes 21 to which a pair of magnets 31 are attached and which guide a magnetic flux generated from the pair of magnets 31. As illustrated in FIG. 1, the optical pickup actuator includes both the internal yokes 23 and the external yokes 21. The supports 16 may be made from wires or leaf springs, and are fixed to the sides 15c and 15d of the lens holder 15. FIG. 1 shows an example of an optical pickup actuator including six wires, all or four of which may be used as the supports 16.

An optical pickup actuator with the pair of magnetic circuits according to the embodiment of the present invention configured as described above is able to perform two-axis, three-axis, and four-axis control. The number of wires used as the supports 16 varies according to which kind of control the optical pickup actuator will be used for. (Here, two-axis, three-axis, and four-axis control has the same meaning as described above.)

Figure 2:
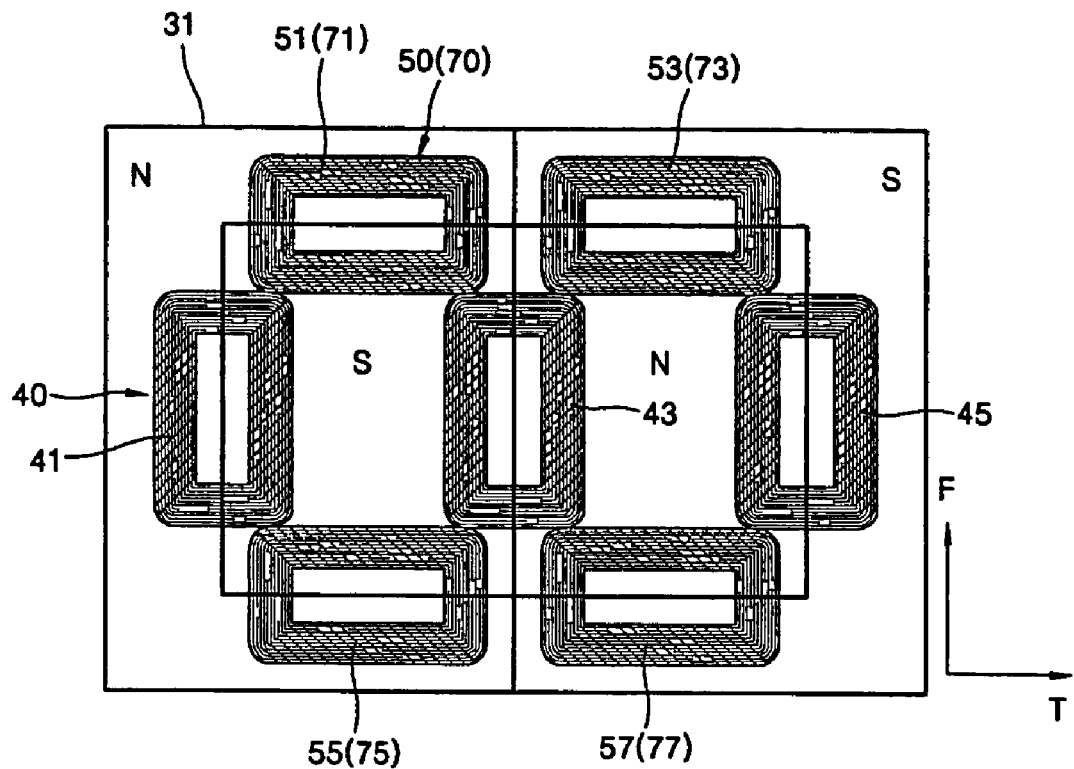
FIG. 2 is a schematic diagram of the magnetic circuit shown in FIG. 1.
Figure 3:
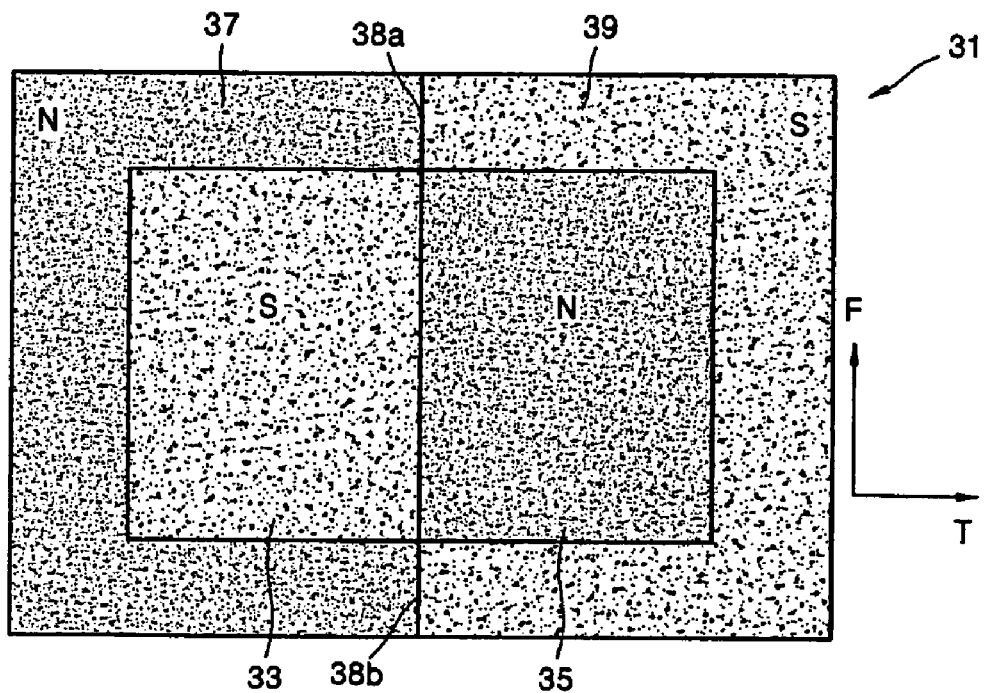
FIG. 3 is a top view of the magnet shown in FIG. 2.

Referring to FIG. 2, each of the pair of magnetic circuits comprises the magnet 31, a tracking coil 40 driving a movable part including the lens holder 15 in the tracking direction T, and a focus coil 50 driving the lens holder 15 in the focus direction F. The magnet 31 is disposed opposite the tracking coil 40 and the focus coil 50. Referring to FIG. 3, the magnet 31 includes first and second magnetic portions 33 and 35 that are adjacent to each other and opposite in polarity, a third magnetic portion 37 that surrounds three sides of the first magnetic portion 33 and has opposite polarity to the same, and a fourth magnetic portion 39 that surrounds three sides of the second magnetic portion 35 and has opposite polarity to the same. As illustrated in FIG. 3, ends of the third magnetic portion 37 are adjacent to ends of the fourth magnetic portion 39.

When viewing toward the tracking coil 40 and the focus coil 50, FIG. 3 shows an example in which the first and fourth magnetic portions 33 and 39 have an S pole while the second and third magnetic portions 35 and 37 have an N pole. Here, the polarities of the first through fourth magnetic portions 33, 35, 37, and 39 may be opposite to those shown in FIG. 3. According to one embodiment, the magnet 31 shown in FIG. 3 is a surface-quadrupole magnet with four simultaneously magnetized poles. Alternatively, the magnet 31 may be formed by attaching a pair of surface two-pole magnets together, either one consisting of the first and third magnetic portions 33 and 37 having opposite polarities and being formed by two-pole magnetization, and the other consisting of the second and fourth magnetic portions 35 and 39 having opposite polarities and being formed by two-pole magnetization.

The tracking coil 40 includes a first tracking coil 41 interacting with the first and third magnetic portions 33 and 37, a second tracking coil 43 interacting with the first and second magnetic portions 33 and 35, and a third tracking coil 45 interacting with the second and fourth magnetic portions 35 and 39. As shown in FIG. 2, the first through third tracking coils 41, 43, and 45 are arranged in one direction, and preferably in the tracking direction T. Two opposing sides of each of the first through third tracking coils 41, 43, and 45 are used as an effective tracking coil.

The focus coil 50 includes first through fourth focus coils 51, 53, 55, and 57. The first and third focus coils 51 and 55 are disposed on either side of the tracking coil 40 in a direction perpendicular to the direction in which the first through third tracking coils 41, 43, and 45 are arranged, and preferably in the focus direction F, so as to interact with the first and third magnetic portions 33 and 37. The second and fourth focus coils 53 and 57 are disposed on either side of the tracking coil 40 in the focus direction F, so as to interact with second and fourth magnetic portions 35 and 39.

Either or both the tracking coil 40 and the focus coil 50 may be made of fine pattern coils that are fabricated by patterning a metal film into the form of a coil. Since the fine pattern coils are thin, it is possible to decrease the weight and size of the movable part of the actuator. FIG. 2 shows an example in which both the tracking coil 40 and the focus coil 50 have been formed on a single film in the form of fine pattern coils.

According to one embodiment, both the tracking coil 40 and the focus coil 50 are multilayer fine pattern coils. That is, each of the first through third tracking coils 41, 43, and 45 are formed to be a stack of multiple layers, e.g., a stack of four layers. And each of the first through fourth focus coils 51, 53, 55, and 57 are formed to be a plurality of layers, e.g., two layers. By interposing an insulating material between coil patterns in the fine pattern coils, it is possible to form a coil pattern with a plurality of layers formed in a stack. Thus, it is highly possible to form the tracking coil 40 and/or the focus coil 50 to have such a multilayer structure.

The magnetic circuit may further include a tilt coil 70. The tilt coil 70 has the same structure as the focus coil 50 and may be arranged at substantially the same position. That is, the tilt coil 70 includes first through fourth tilt coils 71, 73, 75, and 77 that may overlap with the first through fourth focus coils 51, 53, 55, and 57, respectively. Thus, FIG. 2 shows the tilt coil 70 with the same structure as the focus coil 50 and arranged at the same position overlapping the focus coil 50. The tilt coil 70 may be formed of fine pattern coils. Preferably, the tracking coil 40, the focus coil 50, and the tilt coil 70 are all made of fine pattern coils.

In this case, like the tracking coil 40 and the focus coil 50, each of the first through fourth tilt coils 71, 73, 75, and 77 have multiple layers, e.g., two layers, stacked. When the tracking coil 40, the focus coil 50, and the tilt coil 70 are all formed of multilayer fine pattern coils, the simplest method of forming them is to pattern a coil pattern on each layer using the same mask pattern. By using the same method, a coil pattern on each layer may be formed to have the same coil arrangement, as shown in FIG. 2, thus making the number of layers stacked in the focus coil 50 and the tilt coil 70 equal to that in the tracking coil 40. Since the tilt coil 70 overlaps with the focus coil 50, when the tracking coil 40 has four layers, each of the focus coil 50 and the tilt coil 70 has two layers. To further increase focus sensitivity, the focus coil 50 may have three layers while that of the tilt coil 70 contains a single layer.

While the present invention has been described with reference to the focus coil 50 and the tilt coil 70 having a multilayer structure, they may have a single-layer structure. Furthermore, while FIG. 2 shows that the focus coil 50 and the tilt coil 70 do not overlap with the tracking coil 40, the magnetic circuit may be constructed such that the focus coil 50 and the tilt coil 70 overlap with a portion of the tracking coil 40, thereby further decreasing a width in the focus direction F.

The optical pickup actuator having the magnetic circuit described above allows the movable part to be moved in two axis directions, i.e., in the focus directing F and the tracking direction T. In addition, when asynchronous signals having opposite phases are input to the first and third tilt coils 71 and 75 of either magnetic circuit and the second and fourth coils 73 and 77, respectively, it is possible to control motion of the movable part in a radial tilt direction, thereby enabling three-axis motion control. In this case, six wires are needed to input driving current. As described above, the optical pickup actuator with the magnetic circuit allows the movable part to be driven in two- or three-axis directions, i.e., in the focus direction F, the tracking direction T, and the radial tilt direction.

Since the optical pickup actuator includes one pair of magnetic circuits, when an asynchronous signal is input so that an electromagnetic force acts on the magnetic circuits disposed on one side 15a and the opposing side 15b of the bobbin 15 in downward and upward directions, respectively, the optical pickup actuator allows the movable part to be driven in a tangential tilt direction. Thus, by controlling current applied across the first through fourth tilt coils 71, 73, 75, and 77 of the pair of magnetic circuits in this way, it is possible to drive the movable part in four-axis directions.

Furthermore, while the magnetic circuit of the present invention has been described to have a separate focus coil 50 and tilt coil 70, the focus coil 50 may be used for focus control as well as for tilt control.

For example, when tilt driving signals with opposite phases are applied to the first and third focus coils 51 and 55 and the second and fourth focus coils 53 and 57, respectively, so that electromagnetic forces for tilt driving act on the first and third focus coils 51 and 55 and the second and fourth focus coils 53 and 57 in positive and negative focus directions, respectively, it is possible to drive the movable part in a tilt direction. The tilt driving can be performed simultaneously with focus driving by applying the asynchronous tilt driving signal and a focus driving signal having the same phase to the first and third focus coils 52 and 55 and the second and fourth focus coils 53 and 57, respectively, for focus driving. Since the structure of a magnetic circuit in which the focus coil 50 is used for focus control as well as for tilt driving can be inferred from the foregoing description, a description thereof will not be given.

While it is described above that coils are preferably made of fine pattern coils and at least portions of the coils may be bulk coils made of copper wires. Such bulk coils may be installed by increasing the number of turns in a single coil or stacking a plurality of single coils, to achieve the same effect as a multilayer structure of fine pattern coils. The magnetic circuit configured as described above offers significantly improved sensitivity over a conventional magnetic circuit, which will now be demonstrated by taking tracking control as an example.

Figure 4:
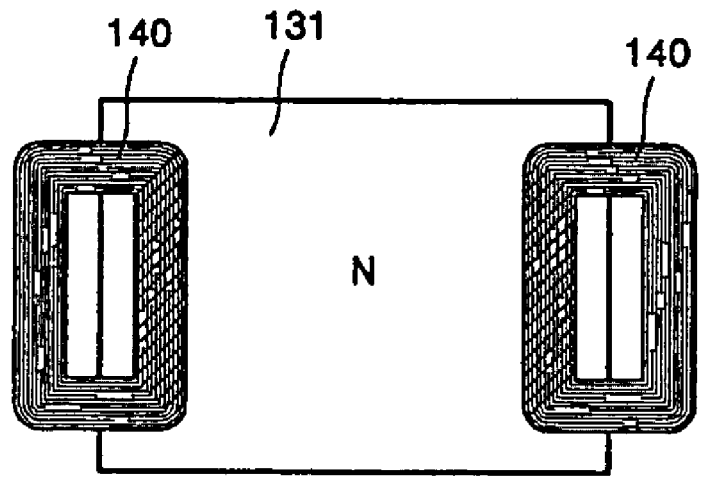
FIG. 4 shows an example of a conventional magnetic circuit.
Figure 5:
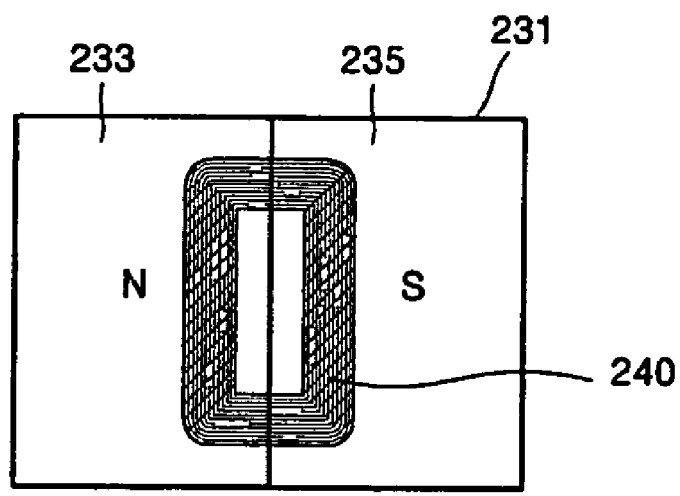
FIG. 5 shows another example of a conventional magnetic circuit.

Recalling the discussion of the conventional magnetic circuits shown in FIGS. 4 and 5, tracking capability can be improved by using at least half of the tracking coil and increasing the number of tracking coils used in tracking control. An embodiment of the present invention can sufficiently satisfy high tracking sensitivity requirements.

For example, even when a coil pattern has a single layer, the magnetic circuit may include three tracking coils 40, two of the four sides of each being used for tracking control. When the fine pattern coils have a multilayer structure, the number of tracking coils 40 can increase by a factor of three.

Thus, the magnetic circuit provides higher tracking sensitivity than is required by a 16-speed recordable DVD, for example, tracking sensitivity of over 150 μm/V. The inventors of the present invention estimate that a tracking sensitivity of about 100±10 μm/V is required to realize a 16-speed recordable DVD. Thus, an embodiment of the present invention is able to provide the tracking sensitivity required by a 16-speed or higher-speed recordable DVD.

Even when a coil pattern has a single layer, the magnetic circuit may include four focus coils 50, two of the four sides of each being used for focus control. When a coil pattern has a multilayer structure, the number of focus coils 50 can increase by a factor of four. Thus, the magnetic circuit according to the present invention can offer high focus sensitivity of over 150 μm/V as well.

Furthermore, even when a coil pattern has a single layer, the magnetic circuit includes four tilt coils, two of the four sides of each being used for tilt control. The same is true when the focus coil 50 is used for both focus and tilt control or when a separate tilt control 70 is used for tilt driving. Thus, the magnetic circuit is able to provide sufficiently high tilt sensitivity as well as highly efficient utilization of the tilt coil 70.

While it is described with reference to FIGS. 1-3 that the optical pickup actuator includes separate magnetic circuit portions for focus driving, tracking driving, and tilt driving, the optical pickup actuator may include only one or two of the described magnetic circuit portions and various changes in the construction of the remaining components may be made. Since the changes in construction can be readily inferred from technology commonly known in the art and the above disclosure, a detailed explanation thereof will not be given.

Figure 6:
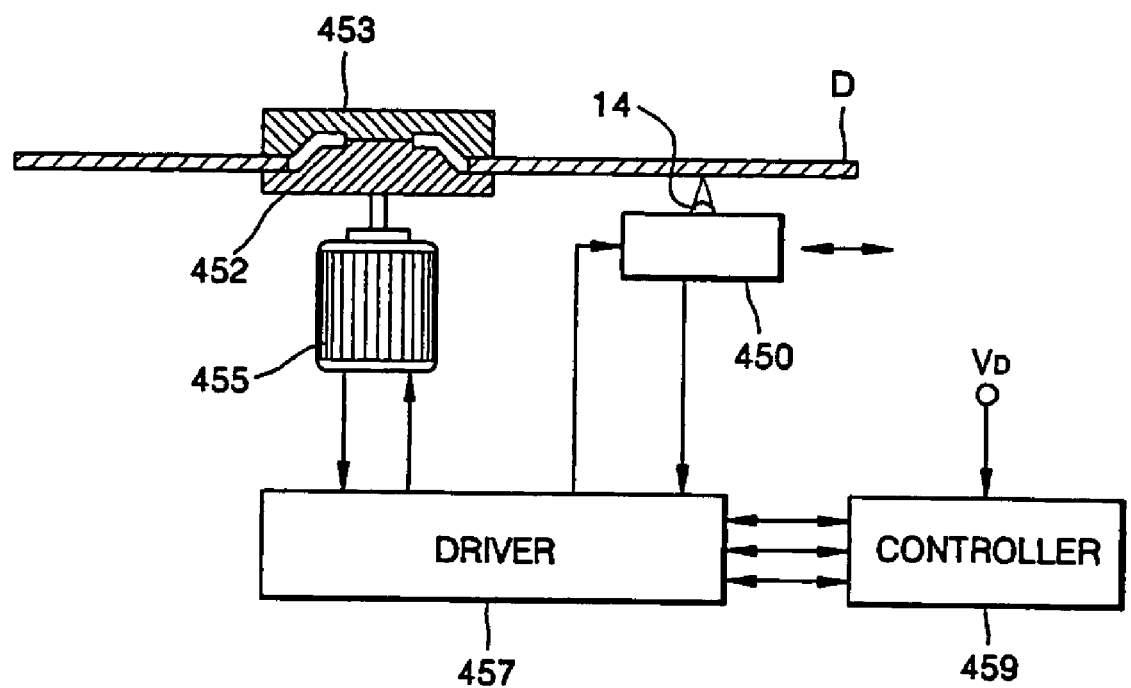
FIG. 6 is a schematic diagram showing the construction of an optical recording and/or reproducing apparatus including an optical pickup actuator according to the present invention.

FIG. 6 is a schematic diagram showing the construction of an optical recording and/or reproducing apparatus including an optical pickup actuator according to an embodiment of the present invention. Referring to FIG. 6, the optical recording and/or reproducing apparatus includes a spindle motor 455 that rotates an optical disc D, which is an optical information storage medium, an optical pickup 450 that is installed capable of movement in a radial direction of the optical disc D and reproduces/records information on the optical disc D, a driver 457 that drives the spindle motor 455 and the optical pickup 450, and a controller 459, with a voltage input VD, that controls focusing, tracking, and/or tilt servos of the optical pickup 450. Here, reference numerals 452 and 453 denote a turntable and a clamp for chucking the optical disc D, respectively.

The optical pickup 450 includes an optical system with the objective lens 14 that focuses a beam emitted by a light source onto the optical disc D, and the optical pickup actuator driving the objective lens 14. The optical pickup actuator includes a magnetic circuit according to an embodiment of the present invention. A beam reflected from the optical disc D is detected by a photodetector mounted in the optical pickup 450 and photoelectrically converted into an electrical signal, which is then input to the controller 459 through the driver 457. The driver 457 controls the rotation speed of the spindle motor 455, amplifies the input signal, and drives the optical pickup 450. The controller 459 sends focus servo, tracking servo, and/or tilt servo commands, which have been adjusted based on the signal received from the driver 457, back to the driver 457 so that the optical pickup can perform focusing, tracking, and/or tilting servo operations.

The optical recording and/or reproducing apparatus can operate at speeds higher than 16-speed for recorable DVDs and speeds higher than 4-speed for BDs. Of course, the optical recording and/or reproducing apparatus can also be used at lower speeds.

The present invention is able to provide the highly sensitive focus control, tracking control, and/or tilt control that are required for high-speed operation.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. A magnetic circuit for an optical pickup actuator, comprising:
    a magnet including first and second magnetic portions that are adjacent to each other and opposite in polarity, and third and fourth magnetic portions that at least partially surround the first and second magnetic portions, respectively, and have opposite polarities to the first and second magnetic portions, respectively;
    a tracking coil unit including first through third tracking coils aligned with one another in a first direction so that each tracking coil interacts with two of the first through fourth magnetic portions; and a focus coil unit that includes first through fourth focus coils, two of which are disposed on opposing sides of the tracking coil unit in a second direction crossing the first direction, to interact with the first and third magnetic portions, and the remaining two of which are disposed on the opposing sides of the tracking coil unit in the second direction to interact with second and fourth magnetic portions.

2. The magnetic circuit of claim 1, wherein the focus coil unit is useable for focus and tilt driving.

3. The magnetic circuit of claim 1, wherein the focus coil unit is made of a fine pattern coil.

4. The magnetic circuit of claim 1, further comprising a tilt coil unit including first through fourth tilt coils that overlap with the first through fourth focus coils, respectively.

5. The magnetic circuit of claim 4, wherein the tilt coil unit is made of a fine pattern coil.

6. The magnetic circuit of claim 1, wherein each of the first through third tracking coils has a multilayer structure.

7. The magnetic circuit of claim 1, wherein the tracking coil unit is made of a fine pattern coil.

8. The magnetic circuit of claim 7, wherein the magnet is one of a surface quadrupole magnet, or a magnet formed by attaching a surface two-pole magnet having the first and third magnetic portions to another surface two-pole magnet having the second and fourth magnetic portions.

9. The magnetic circuit of claim 1, wherein the magnet is one of a surface quadrupole magnet, or a magnet formed by attaching a surface two-pole magnet having the first and third magnetic portions to another surface two-pole magnet having the second and fourth magnetic portions.

10. A magnetic circuit for an optical pickup actuator, comprising:
a magnet including first and second magnetic portions that are adjacent to each other and opposite in polarity, and third and fourth magnetic portions that at least partially surround the first and second magnetic portions, respectively, and have opposite polarities to the first and second magnetic portions, respectively; and
a focus coil unit that includes first through fourth focus coils, two of which are disposed in a focus direction to interact with the first and third magnetic portions, and the remaining two of which are disposed in the focus direction to interact with second and fourth magnetic portions.

11. The magnetic circuit of claim 10, wherein each of the first through fourth focus coils has a multilayer structure.

12. The magnetic circuit of claim 10, wherein the focus coil unit is useable for focus and tilt driving.

13. The magnetic circuit of claim 10, further comprising:
a tilt coil unit including first through fourth tilt coils that overlap with the first through fourth focus coils, respectively.

14. The magnetic circuit of claim 13, wherein each of the first through fourth tilt coils has a multilayer structure.

15. The magnetic circuit of claim 14, wherein the tilt coil unit is made of a fine pattern coil.

16. The magnetic circuit of claim 10, wherein the tilt coil unit is made of a fine pattern coil.

17. An optical recording and/or reproducing apparatus comprising:
an optical pickup that has an actuator driving an objective lens, which is installed capable of movement along a radial direction of an optical information storage medium, and which reproduces and/or records information on the optical information storage medium; and
a controller that controls servos of the optical pickup,
wherein the actuator comprises
a lens holder holding the objective lens,
a plurality of supports that support the lens holder movably with respect to a base, each of the supports having a first end attached to one of two opposing sides of the lens holder and a second end fixed to a holder mounted on one side of the base, and
a pair of magnetic circuits disposed opposite each other on remaining opposing sides of the lens holder, to which the supports are not attached, and the base, and
wherein at least one of the pair of magnetic circuits comprises
a magnet including first and second magnetic portions that are adjacent to each other and opposite in polarity, and third and fourth magnetic portions that at least partially surround the first and second magnetic portions, respectively, and have opposite polarities to the first and second magnetic portions, respectively,
a tracking coil unit including first through third tracking coils aligned with one another in a first direction so that each tracking coil interacts with two of the first through fourth magnetic portions, and
a focus coil unit that includes first through fourth focus coils, two of which are disposed on opposing sides of the tracking coil unit in a second direction crossing the first direction, to interact with the first and third magnetic portions, and the remaining two of which are disposed on the opposing sides of the tracking coil unit in the second direction to interact with the second and fourth magnetic portions.

18. The apparatus of claim 17, wherein the focus coil unit is useable for focus and tilt driving.

19. The apparatus of claim 17, wherein the focus coil unit is made of a fine pattern coil.

20. The apparatus of claim 17, wherein the magnetic circuit further comprises:
a tilt coil unit including first through fourth tilt coils that overlap with the first through fourth focus coils, respectively.

21. The apparatus of claim 20, wherein the tilt coil unit is made of a fine pattern coil.

22. The apparatus of claim 17, wherein each of the first through third tracking coils has a multilayer structure.

23. The apparatus of claim 17, wherein the tracking coil unit is made of a fine pattern coil.

24. The apparatus of claim 17, wherein the magnet is one of a surface-quadrupole magnet, or a magnet formed by attaching a surface two-pole magnet having the first and third magnetic portions to another surface two-pole magnet having the second and fourth magnetic portions.

25. An optical recording and/or reproducing apparatus comprising:
an optical pickup that has an actuator driving an objective lens, which is installed capable of movement along a radial direction of an optical information storage medium, and which reproduces and/or records information on the optical information storage medium; and
a controller that controls servos of the optical pickup,
wherein the actuator comprises
a lens holder holding the objective lens,
a plurality of supports that support the lens holder movably with respect to a base, each of the supports having a first end attached to one of two opposing sides of the lens holder and a second end fixed to a holder mounted on one side of the base, and a pair of magnetic circuits disposed opposite each other on remaining opposing sides of the lens holder, to which the supports are not attached, and the base, and wherein at least one of the pair of magnetic circuits comprises a magnet including first and second magnetic portions that are adjacent to each other and opposite in polarity, and third and fourth magnetic portions that at least partially surround the first and second magnetic portions and have opposite polarities to the first and second magnetic portions, respectively; and a focus coil unit that includes first through fourth focus coils, two of which are disposed in a focus direction to interact with the first and third magnetic portions, and the remaining two of which are disposed in the focus direction to interact with second and fourth magnetic portions.

26. The apparatus of claim 25, wherein each of the first through fourth focus coils has a multilayer structure.

27. The apparatus of claim 25, wherein the focus coil unit is useable for focus and tilt driving.

28. The apparatus of claim 25, wherein the magnetic circuit further comprises:

a tilt coil unit including first through fourth tilt coils that overlap with the first through fourth focus coils, respectively.

29. The apparatus of claim 28, wherein each of the first through fourth tilt coils has a multilayer structure.

30. The apparatus of claim 29, wherein the tilt coil unit is made of a fine pattern coil.

31. The apparatus of claim 25, wherein the focus coil unit is made of a fine pattern coil.

32. The apparatus of claim 25, wherein the magnet is one of a surface-quadrupole magnet, or a magnet formed by attaching one surface two-pole magnet having the first and third magnetic portions to another surface two-pole magnet having the second and fourth magnetic portions.

33. A magnetic circuit for an optical pickup actuator, comprising:

a magnet including first and second magnetic portions disposed adjacent to each other and opposite in polarity, and third and fourth magnetic portions that at least partially surround the first and second magnetic portions, respectively, and have opposite polarities to the first and second magnetic portions, respectively; and at least one of a tracking coil unit including first through third tracking coils aligned with one another in a first direction so that each tracking coil interacts with two of the first through fourth magnetic portions, and a focus coil unit that includes first through fourth focus coils, two of which are arranged in a second direction approximately perpendicular to the first direction, to interact with the first and third magnetic portions, and the remaining two of which are arranged in the second direction to interact with second and fourth magnetic portions.

34. The magnetic circuit of claim 33, wherein the focus coil unit is useable for focus and tilt driving.

35. The magnetic circuit of claim 33, wherein the focus coil unit is made of a fine pattern coil.

36. The magnetic circuit of claim 33, wherein the tracking coil unit is made of a fine pattern coil.

37. The magnetic circuit of claim 33, further comprising a tilt coil unit including first through fourth tilt coils arranged to overlap with the first through fourth focus coils, respectively.

38. The magnetic circuit of claim 37, wherein the tilt coil unit is made of a fine pattern coil.

39. The magnetic circuit of claim 37, wherein each of the first through fourth tilt coils has a multilayer structure.

40. The magnetic circuit of claim 33, wherein each of the first through third tracking coils has a multilayer structure.

41. The magnetic circuit of claim 33, wherein each of the first through fourth focus coils has a multilayer structure.

42. The magnetic circuit of claim 33, wherein the magnet is one of a surface quadrupole magnet, or a magnet formed by attaching a surface two-pole magnet having the first and third magnetic portions to another surface two-pole magnet having the second and fourth magnetic portions.

43. An optical recording and/or reproducing apparatus comprising:

an actuator, driving an objective lens, and being positioned on an optical pickup to reproduce and/or record information from and/or on an optical information storage medium, the actuator comprising a lens holder holding the objective lens, a plurality of supports movably supporting the lens holder with respect to a base, each of the supports having a first end attached to one of two opposing sides of the lens holder and a second end fixed to a holder mounted on a first side of the base, and a pair of the magnetic circuits of claim 35, each of the respective tracking coil units and/or each of the respective focus coil units being disposed on one of opposing sides of the lens holder on which the supports are not attached, and the respective magnets being disposed on the base opposite the respective tracking coil units and/or the respective focus coil units.

* * * * *